United States Patent [19]

Berg et al.

[11] Patent Number: 4,601,791
[45] Date of Patent: Jul. 22, 1986

[54] SEPARATION OF N-PROPANOL FROM ALLYL ALCOHOL BY EXTRACTIVE DISTILLATION

[76] Inventors: Lloyd Berg; Mark G. Vosburgh, both of 1314 S. Third Ave., Bozeman, Mont. 59715

[21] Appl. No.: 755,302

[22] Filed: Jul. 15, 1985

[51] Int. Cl.$^4$ .............................................. B01D 3/40
[52] U.S. Cl. ...................................... 203/51; 203/58; 203/60; 203/63; 203/57; 568/913
[58] Field of Search ...................... 203/51, 57, 58, 60, 203/64, 63, 52, 56; 568/913

[56] References Cited

U.S. PATENT DOCUMENTS

| | | | |
|---|---|---|---|
| 2,433,323 | 12/1947 | Reiter et al. | 203/60 |
| 2,485,694 | 10/1949 | Burchfield | 203/88 |
| 2,570,205 | 10/1951 | Carlson et al. | 568/913 |
| 2,663,679 | 12/1953 | Drout, Jr. | 203/84 |
| 2,663,680 | 12/1953 | Robertson | 203/84 |

FOREIGN PATENT DOCUMENTS 0967471  8/1964  United Kingdom ................. 203/60

OTHER PUBLICATIONS

Chemical Abstract, Filip et al., "Separation of Allyl Alcohol from N-propyl Alcohol by Extractive Rectification", vol. 81, 1974, p. 419.

Chemical Abstract, Filip et al., "Separation of Allyl and Propyl Alcohols by Extractive Fractionation"; vol. 80, 1974, p. 375.

Primary Examiner—S. Leon Bashore
Assistant Examiner—V. Manoharan

[57] ABSTRACT

N-propanol and allyl alcohol cannot be separated from each other by distillation because of the proximity of their boiling points. N-propanol can be readily separated from allyl alcohol by using extractive distillation in which the extractive agent is a higher boiling oxygenated, nitrogenous and/or sulfur containing organic compound or a mixture of two or more of these compound. Examples of effective agents are: dimethylsulfoxide; acetamide and ethylene glycol phenylether; adiponitrile; N,N-dimethylacetamide; dimethylformamide; and sulfolane.

2 Claims, No Drawings

SEPARATION OF N-PROPANOL FROM ALLYL ALCOHOL BY EXTRACTIVE DISTILLATION

FIELD OF THE INVENTION

This invention relates to a method for separating n-propanol from allyl alcohol using certain higher boiling liquids as the extractive agent in extractive distillation.

DESCRIPTION OF PRIOR ART

Extractive distillation is the method of separating close boiling compounds by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

n-Propanol is one of the more common of organic solvents in commercial use today. Where ever practical, it is mandatory to recover the solvent and re-use it. Frequently the n-propanol ends up in a mixture with other solvents and must be separated and purified before it is suitable to be used again. One of the most troublesome components of a solvent mixture containing n-propanol is allyl alcohol. The allyl alcohol can originate from other sources or it can be caused by the dehydrogenation of some of the n-propanol. n-Propanol boils at 97.2° C., allyl alcohol at 97.1° C. and thus are impossible to separate by conventional rectification. Their relative volatility is 1.01.

Extractive distillation would be an attractive method of effecting the separation of allyl alcohol from n-propanol if agents can be found that (1) will alter the relative volatility between allyl alcohol and n-propanol, (2) form no azeotropes with allyl alcohol or n-propanol and (3) are easy to recover from allyl alcohol, that is boil sufficiently above allyl alcohol to make the separation by rectification possible with only a few theoretical plates.

Extractive distillation typically requires the addition of an equal amount to twice as much extractive agent as the allyl alcohol-n-propanol on each plate in the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with allyl alcohol otherwise it will form a two phase azeotrope with the allyl alcohol in the recovery column and some other method of separation will have to be employed.

N. C. Robertson, U.S. Pat. No. 2,663,680, Dec. 22, 1953, described an azeotropic distillation process to separate allyl alcohol from n-propanol using water as the azeotrope former. S. Filip & Z. Lugoski, Pr. Nauk, 1974, 21(9), 45–58 (Polish) considered a number of compounds to break up allyl alcohol-n-propanol-water mixtures. These are azeotropic distillation processes, not extractive distillation.

OBJECTIVE OF THE INVENTION

The object of this invention is to provide a process or method of extractive distillation that will enhance the relative volatility of n-propanol from allyl alcohol in their separation in a rectification column. It is a further objective of this invention to identify organic compounds which are stable, can be separated from n-propanol by rectification with relatively few plates and can be recycled to the extractive distillation column and re-used with little decomposition.

SUMMARY OF THE INVENTION

The objects of this invention are provided by a process for separating n-propanol from allyl alcohol which entails the use of certain oxygenated, nitrogenous and-/or sulfur containing organic compounds as the agent in extractive distillation.

DETAILED ELABORATION OF THE INVENTION

We have discovered that certain oxygenated, nitrogenous and/or sulfur containing organic compounds, some individually but principally as mixtures, will effectively enhance the relative volatility between

TABLE 1

| Extractive Agents Which Contain Dimethylsulfoxide (DMSO) | | | | |
|---|---|---|---|---|
| Compounds | Ratios | | Relative Volatilities | |
| None |  |  | 1.01 |  |
| Dimethylsulfoxide (DMSO) | 1 | 6/5 | 1.38 | 1.43 |
| DMSO, Dimethylformamide | $(\frac{1}{2})^2$ | $(3/5)^2$ | 1.47 | 1.46 |
| DMSO, Ethylene glycol | " | " | 1.25 | 1.31 |
| DMSO, 1,4-Butanediol | " | " | 1.32 | 1.30 |
| DMSO, Acetamide | " | " | 1.43 | 1.40 |

TABLE 1-continued

Extractive Agents Which Contain Dimethylsulfoxide (DMSO)

| Compounds | Ratios | | Relative Volatilities | |
|---|---|---|---|---|
| DMSO, Adiponitrile | " | " | 1.48 | 1.52 |
| DMSO, Sulfolane | " | " | 1.42 | 1.39 |
| DMSO, Dihydroxyphenyl sulfone | " | " | 1.36 | 1.36 |
| DMSO, 4,4'-Sulfonyldiphenol | " | " | 1.21 | 1.29 |
| DMSO, N,N—Dimethylacetamide | " | " | 1.30 | 1.37 |
| DMSO, Dimethylformamide (DMFA), Ethylene glycol | $(\frac{2}{3})^3$ | (4/5) | 1.38 | |
| DMSO, DMFA, 1,4-Butanediol | " | " | 1.35 | 1.31 |
| DMSO, DMFA, Acetamide | " | " | 1.45 | 1.47 |
| DMSO, DMFA, N,N—Dimethylacetamide | " | " | 1.35 | 1.34 |
| DMSO, DMFA, Adiponitrile | " | " | 1.47 | 1.42 |
| DMSO, DMFA, Sulfolane | " | " | 1.45 | 1.46 |
| DMSO, Acetamide, N,N—Dimethylacetamide | " | " | 1.44 | 1.47 |
| DMSO, Acetamide, Ethylacetoacetate | " | " | 1.43 | 1.42 |
| DMSO, Acetamide, Adiponitrile | " | " | 1.50 | 1.45 |
| DMSO, Adiponitrile, Sulfolane | " | " | 1.56 | 1.50 |
| DMSO, Adiponitrile, N,N—Dimethylacetamide | " | " | 1.48 | 1.51 |
| DMSO, 4,4'-Sulfonyldiphenol | " | " | 1.36 | 1.17 |
| DMSO, Adiponitrile, Dihydroxyphenyl sulfone | " | " | 1.35 | 1.30 |

TABLE 2

Extractive Agents Which Contain Dimethylformamide (DMFA)

| Compounds | Ratios | | Relative Volatilities | |
|---|---|---|---|---|
| Dimethylformamide (DMFA) | 1 | | 1.35 | |
| DMFA, Ethylene glycol | $(\frac{1}{2})^2$ | $(3/5)^2$ | 1.22 | 1.29 |
| DMFA, Acetamide | " | " | 1.36 | 1.40 |
| DMFA, N,N—Dimethylacetamide | " | " | 1.41 | 1.38 |
| DMFA, Adiponitrile | " | " | 1.34 | 1.37 |
| DMFA, Sulfolane | " | " | 1.37 | 1.32 |
| DMFA, Adiponitrile, N,N—Dimethylacetamide | " | " | 1.40 | 1.38 |
| DMFA, Acetamide, N,N—Dimethylacetamide | " | " | 1.34 | 1.39 |
| DMFA, Acetamide, Polyethylene glycol | " | " | 1.34 | 1.31 |
| DMFA, Acetamide, Sulfolane | " | " | 1.40 | 1.37 |
| DMFA, Sulfolane, N,N—Dimethylacetamide | " | " | 1.34 | 1.41 |

TABLE 3

Extractive Agents Whcih Contain Acetamide

| Compounds | Ratios | | Relative Volatilities | |
|---|---|---|---|---|
| Acetamide | 1 | 6/5 | 1.29 | 1.23 |
| Acetamide, n-Hexanol | $(\frac{1}{2})^2$ | $(3/5)^2$ | 1.20 | 1.17 |
| Acetamide, Glyceryl triacetate | " | " | 1.36 | 1.33 |
| Acetamide, Ethylene glycol phenyl ether | " | " | 1.27 | 1.26 |
| Acetamide, Ethylene glycol diacetate | " | " | 1.36 | 1.30 |
| Acetamide, Ethylacetoacetate | " | " | 1.22 | 1.32 |
| Acetamide, Adiponitrile | " | " | 1.46 | 1.38 |
| Acetamide, Sulfolane | " | " | 1.29 | 1.31 |
| Acetamide, N,N—Dimethylacetamide | " | " | 1.31 | 1.24 |
| Acetamide, N,N—Dimethylacetamide, Sulfolane | $(\frac{2}{3})^3$ | $(4/5)^3$ | 1.38 | 1.34 |

TABLE 4

Miscellaneous Extractive Agents Which Are Effective

| Compounds | Ratios | | Relative Volatilities | |
|---|---|---|---|---|
| Adiponitrile | 1 | 6/5 | 1.34 | 1.34 |
| 1,4-Butanediol | " | — | 1.13 | |
| N,N—Dimethylacetamide | " | " | 1.31 | 1.33 |
| Sulfolane | " | " | 1.22 | 1.14 |
| Adiponitrile, N,N—Dimethylacetamide | $(\frac{1}{2})^2$ | $(3/5)^2$ | 1.33 | 1.41 |
| Adiponitrile, Sulfolane | " | " | 1.42 | 1.47 |
| Sulfolane, N,N—Dimethylacetamide | " | " | 1.39 | 1.40 |
| Phthalic anhydride, Maleic anhydride, Diethylmaleate | $(\frac{2}{3})^3$ | $(4.5)^3$ | 1.27 | 1.28 |

TABLE 5

Data From Runs Made in Rectification Column.

| Agent | Time min. | Overhead Temp. °C. | Stillpot Temperature °C. | | Weight % Overhead | n-propanol Bottoms | Relative Volatilities |
| --- | --- | --- | --- | --- | --- | --- | --- |
| | | | At Start | When Sampling | | | |
| DMSO | 60 | 98.4 | 99.4 | 143.2 | 91.1 | 60.3 | 1.53 |
| " | 90 | 96.0 | 99.4 | 152.0 | 91.3 | 60.6 | 1.53 |
| " | 120 | 94.0 | 99.4 | 158.0 | 92.4 | 60.4 | 1.59 |
| | | | | | | | 1.55 average |
| DMFA | 60 | 105.8 | 96.2 | 126.4 | 89.9 | 61.1 | 1.47 |
| " | 90 | 103.6 | 96.2 | 131.6 | 92.9 | 62.4 | 1.58 |
| " | 120 | 104.4 | 96.2 | 134.6 | 91.5 | 62.2 | 1.52 |
| | | | | | | | 1.52 average | n-propanol and allyl alcohol and permit the separation of pure n-propanol from allyl alcohol by rectification when employed as the agent in extractive distillation. Table 1 lists dimethylsulfoxide, its mixtures and approximate proportions that we have found to be effective. Table 2 is a similar listing for dimethylformamide, Table 3 for acetamide and Table 4 for a few otherwise unclassified compounds. The data in Tables 1, 2, 3 and 4 were obtained in a vapor-liquid equilibrium still. In each case, the starting material was the 50—50% allyl alcohol—n-propanol mixture. The ratios are the parts of extractive agent used per part of allyl alcohol-n-propanol mixture. The relative volatilities are listed for each of the two ratios employed.

The compounds that are effective as extractive distillation agents when used alone are dimethylsulfoxide (DMSO), dimethylformamide (DMFA), acetamide, adiponitrile, N,N-dimethylacetamide and sulfolane. The compounds which are effective when used in mixtures of two or more components are ethylene glycol, polyethylene glycol, ethylene glycol phenyl ether, ethylene glycol diacetate, dihydroxyphenyl sulfone, 4,4'-sulfonyldiphenol, ethyl acetoacetate, n-hexanol, 1,4-butanediol, glyceryl triacetate, diethyl maleate, phthalic anhydride and maleic anhydride. The ratios in Tables 1, 2, 3 and 4 are the parts of extractive agent used per part of n-propanol-allyl alcohol mixture. The two relative volatilities correspond to the two different ratios. For example in Table 1, one part of DMSO with one part of n-propanol-allyl alcohol mixture gives a relative volatility of 1.38, 6/5 parts of DMSO gives 1.43. One half part of DMSO mixed with one half part of adiponitrile with one part of n-propanol-allyl alcohol mixture gives a relative volatility of 1.48, 3/5 parts of DMSO plus 3/5 parts of adiponitrile gives 1.52. One third parts of DMSO plus ⅓ parts of adiponitrile plus ⅓ parts of N,N-dimethylacetamide mixed with one part of n-propanol-allyl alcohol mixture gives a relative volatility of 1.48, with 2/5 parts, these three give 1.51.

In every example in Table 1,2, 3 and 4 the starting material is a 50—50% mixture of n-propanol and allyl alcohol which possesses a relative volatility of 1.01.

Two of the compounds listed in Table 1 and 2 and whose relative volatility had been determined in the vapor-liquid equilibrium still, were then evaluated in a glass perforated plate rectification column possessing 4.5 theoretical plates. The results are listed in Table 5. The n-propanol-allyl alcohol mixture used contained 65% n-propanol. In both cases the feed or bottoms contained less than 65% n-propanol and the overhead contained more than 90% n-propanol. Without the extractive agent, the overhead would be about 65% n-propanol, virtually the same as the bottoms. The first line in Table 5 is the result obtained after one hour operation with from one to two parts of extractive agent per part of allyl alcohol-n-propanol mixture being boiled up to the condenser. The second line is the result after 1.5 hours which is usually the maximum time required for the equipment to come to equilibrium. The third line is the result after two hours of total operating time and in both cases indicates that equilibrium through-out the column had been achieved.

THE USEFULNESS OF THE INVENTION

The usefulness or utility of this invention can be demonstrated by referring to the data presented in Tables 1, 2, 3, 4 and 5. All of the successful extractive distillation agents show that n-propanol can be removed from allyl alcohol by means of distillation in a rectification column and that the ease of separation as measured by relative volatility is considerable. Without these extractive distillation agents, virtually no improvement will occur in the rectification column. The data also show that the most attractive agents will operate at a boilup rate low enough to make this a useful and efficient method of recovering high purity n-propanol from any mixture with allyl alcohol. The stability of the compounds used and the boiling point difference is such that complete recovery and recycle is obtainable by a simple distillation and the amount required for make-up is small.

WORKING EXAMPLES

EXAMPLE 1

Thirty-five grams of n-propanol 15 grams of allyl alcohol and fifty grams of dimethylsulfoxide (DMSO) were charged to an Othmer type glass vapor-liquid equilibrium still and refluxed for fifteen hours. Analysis of the vapor and liquid by gas chromatography gave vapor composition 68.3% n-propanol, 31.7% allyl alcohol; liquid of 61.4% n-propanol, 38.6% allyl alcohol. This indicates a relative volatility of 1.38. Ten grams of DMSO were added and refluxing continued for another ten hours. Analysis indicated a vapor composition of 68.9% n-propanol, 31.1% allyl alcohol; a liquid composition of 60.8% n-propanol, 39.2% allyl alcohol which is a relative volatility of 1.43.

EXAMPLE 2

Fifty grams of the n-propanol-allyl alcohol mixture, 25 grams of DMSO and 25 grams of adiponitrile were charged to the vapor-liquid equilibrium still and refluxed for twelve hours. Analysis indicated a vapor composition of 63.4% n-propanol, 36.6% allyl alcohol; a liquid composition of 53.9% n-propanol, 46.1% allyl alcohol which is a relative volatility of 1.48. Five grams of DMSO and five grams of adiponitrile were added and refluxing continued for another ten hours. Analysis indicated a vapor composition of 63% n-propanol, 37% allyl alcohol; a liquid composition of 52.8% n-propanol, 47.2% allyl alcohol which is a relative volatility of 1.52.

EXAMPLE 3

Fifty grams of the n-propanol-allyl alcohol mixture 17 grams of DMSO, 17 grams of dimethylformamide (DMFA) and 17 grams of sulfolane were charged to the vapor-liquid equilibrium still and refluxed for five hours. Analysis indicated a vapor composition of 49.1% n-propanol, 50.9% allyl alcohol; a liquid composition of 40% n-propanol, 60% allyl alcohol which is a relative volatility of 1.45. Three grams each of DMSO, DMFA and sulfolane were added and refluxing continued for another six hours. Analysis indicated a vapor composition of 51.6% n-propanol, 48.4% allyl alcohol and a liquid composition of 42.2% n-propanol, 57.8% allyl alcohol which is a relative volatility of 1.46.

EXAMPLE 4

A glass perforated plate rectification column was calibrated with ethylbenzene and p-xylene which possesses a relative volatility of 1.06 and found to have 4.5 theoretical plates. A solution of 200 grams of n-propanol and 200 grams of allyl alcohol was placed in the stillpot and heated. When refluxing began, an extractive agent consisting of pure DMSO was pumped into the column at a rate of 20 ml/min. The temperature of the extractive agent as it entered the column was 90°–100° C. After establishing the feed rate of the extractive agent, the heat input to the n-propanol-allyl alcohol in the stillpot was adjusted to give a reflux rate of 10–20 ml/min. After one hour of operation, overhead and bottoms samples of approximately two ml. were collected and analysed using gas chromatography. The overhead analysis was 91.1% n-propanol, 8.9% allyl alcohol. The bottoms analysis was 60.3% n-propanol, 39.7% allyl alcohol. Using these compositions in the Fenske equation, with the number of theoretical plates in the column being 4.5, gave an average relative volatility of 1.53 for each theoretical plate. After 1.5 hours of total operating time, the overhead and bottoms samples were again taken and analysed. The overhead composition was 91.3% n-propanol, 8.7% allyl alcohol and the bottoms composition was 60.6% n-propanol and 39.4% allyl alcohol. This gave an average relative volatility of 1.53 for each theoretical plate. After two hours of total operating time, the overhead and bottoms samples were again taken and analysed. The overhead composition was 92.4% n-propanol, 7.6% allyl alcohol and the bottoms composition was 60.4% n-propanol, 39.6% allyl alcohol. This gave an average relative volatility of 1.59 for each theoretical plate.

EXAMPLE 5

A solution of 200 grams of n-propanol and 200 grams of allyl alcohol was placed in the stillpot of the same column used in example 4 and heat applied. When refluxing began, an extractive agent comprising pure dimethylformamide (DMFA) was fed to the top of the column at a feed rate of 20 ml/min. and a temperature of 70°–90° C. After establishing the feed rate of the extractive agent, the heat input to the n-propanol-allyl alcohol in the stillpot was adjusted to give a total reflux rate of 10–20 ml/min. Having established the reflux rate, the column was allowed to operate for one hour. After one hour of steady operation, overhead and bottoms samples of approximately two ml. were collected and analysed by gas chromatography. The overhead analysis was 89.9% n-propanol, 10.1% allyl alcohol, the bottoms analysis was 61.1% n-propanol, 38.9% allyl alcohol. Using these compositions in the Fenske equation with the number of theoretical plates in the column being 4.5, gave an average relative volatility of 1.47 for each theoretical plate. After 1.5 hours of total operation, the overhead composition was 92.9% n-propanol, 7.1% allyl alcohol and the bottoms composition was 62.4% n-propanol, 37.6% allyl alcohol. This gave an average relative volatility of 1.58 for each theoretical plate. After two hours of total operation, the overhead composition was 91.5% n-propanol, 8.5% allyl alcohol and the bottoms composition was 62.2% n-propanol, 37.8% allyl alcohol. This gave an average relative volatility of 1.52 for each theoretical plate.

What is claimed is:

1. A method for recovering n-propanol from a mixutre of n-propanol and allyl alcohol which comprises distilling a mixture of n-propanol and allyl alcohol in a rectification column in the presence of about one part of extractive agent per part of n-propanol-allyl alcohol mixture, recovering n-propanol as overhead product, obtaining the allyl alcohol and the extractive agent from the stillpot, separating the allyl alcohol from the extractive agent by distillation in another rectification column, wherein said extractive agent comprises at least one member of the group consisting of acetamide, N,N-dimethylacetamide, adiponitrile, dimethylformamide, dimethylsulfoxide and sulfolane.

2. The process of claim 1 wherein the extractive agent comprises a mixture of acetamide and at least one material from the group consisting of glyceryl triacetate, ethylene glycol phenyl ether, ethylene glycol diacetate, n-hexanol, and ethylacetoacetate.

* * * * *